(12) United States Patent
Yu

(10) Patent No.: US 6,506,403 B1
(45) Date of Patent: Jan. 14, 2003

(54) TREATMENT PATCH

(76) Inventor: Qi Yu, 2446 San Gabriel Blvd., Unit A, Rosemead, CA (US) 91770

( * ) Notice: Subject to any disclaimer, the term of this patent is extended or adjusted under 35 U.S.C. 154(b) by 0 days.

(21) Appl. No.: 09/934,790

(22) Filed: Aug. 21, 2001

(51) Int. Cl.[7] ................................................. A61K 9/70
(52) U.S. Cl. ........................ 424/443; 424/400; 424/445; 424/448
(58) Field of Search ................................ 424/400, 443, 424/445, 448

(56) References Cited

U.S. PATENT DOCUMENTS

| | | | | |
|---|---|---|---|---|
| 4,391,270 A | * | 7/1983 | Uragami | 600/15 |
| 4,798,194 A | * | 1/1989 | Amishima | 335/302 |
| 5,662,925 A | * | 9/1997 | Ebert et al. | 424/447 |
| 5,792,176 A | * | 8/1998 | Chang | 128/898 |
| 5,800,402 A | * | 9/1998 | Bierman | 128/DIG. 26 |
| 6,344,021 B1 | * | 2/2002 | Juster et al. | 600/15 |

* cited by examiner

Primary Examiner—Jose' G. Dees
Assistant Examiner—Konata M. George
(74) Attorney, Agent, or Firm—Raymond Y. Chan; David & Raymond Patent Group

(57) ABSTRACT

A treatment patch includes a patch body having a contacting surface for placing on a skin surface of a treating tissues of a user, and a dressing layer which is provided on the contacting surface containing positively charged metallic ions for depolarizing negative ions accumulated under the skin surface of the treating tissues, wherein a far infrared ray emitter disposed on the. patch body for emitting far infrared rays penetrating into the treating tissues through the skin surface so as to provide an ion passway between the skin surface in contact with the dressing layer of the patch body and the treating tissues so as to enhance the depolarization of the positively charged ions of the dressing layer with the negative ions around the treating tissues of the user to relieve pain.

40 Claims, 4 Drawing Sheets

TREATMENT PATCH

BACKGROUND OF THE PRESENT INVENTION

1. Field of Invention

The present invention relates to a therapeutic application, and more particularly to a treatment patch which provides positively-charged ions fro depolarizing a negatively charged muscular tissues under the human skin so as to efficiently relieve muscle and joint pain.

2. Description of Related Arts

Nowadays, people are suffering from sports injuries and muscle and joint pains in the knees, elbows, hands, backs, shoulders, and etc.. Most people are addicted to pain reliever as such "Tylenol" and "Advil" as their habit for their remedy of pain.

Pain is thought to be associated with imbalances or blockages in energy flow through the body. In order to effectively alleviate pain, pain mechanisms in the human body must be recognized. Pain is transmitted along nerve cells as an electric signal. While quiescent, the nerve has a small charge of about–70 mV. A pain signal depolarizes a cell.

The most common ways in the treatment for pain are heat and magnetic therapy. When the heat is applied on the human skin where the pain is located, the blood vessels are expanded for enhancing the blood circulation. However, many people have allergy due to the heat treatment.

A kind of magnetic patch contains a rare earth magnet coated with purified zinc are prealigned and attached to self-adhesive microporous tape to ensure the correct magnetic pole is in contact with the body. Such magnetic patch functions as an electromagnetic transmitter to emit tiny pulses of energy and generate bioelectromagnetic fields, including magnetic field, micro-electric field and induced current field, which affect the flow of electromagnetic energy in parts of the body. It is claimed that the bioelectromagnetic therapy acts on nerve and muscle cells to relieve pain, relax tense muscles, improve the circulation, and boost immunity.

However, the muscle and joint pain occurs 2 to 4 cm under the skin that general magnetic field may not strong enough to penetrate through the human skin to affect the flow of electromagnetic energy around the joint of the body. However, it is unreasonable to expose a human body under such strong magnetic field condition since clinical experiences report that an improper use of magnetic field may also accelerate the growth of cancer cells and viruses as well as increase the amount of bleeding in the wound. Besides, most people are sensitive to the magnetic field. However, human body should not depend on those pain relievers since the human body may immune to the pain relievers and require higher dosages thereof.

SUMMARY OF THE PRESENT INVENTION

A main object of the present invention is to provide a treatment patch which comprises a dressing layer containing positively charged metallic ions for depolarizing the negative ions in a treating tissue of the muscle or joint to relieve muskulo-skeletal pain, wherein the dressing layer further emits far infrared rays to create an ion passway between the skin in contact with the dressing layer of the treatment patch and the treating tissue so as to enhance the depolarization of the positively charged ions of the dressing layer with the negative ions in the treating tissue of muscle or joint.

Another object of the present invention is to provide a treatment patch wherein neither magnetic field nor external substance is used and permeated into the human body, so that it is safe to use with allergy free.

Accordingly, in order to accomplish the above objects, the present invention provides a treatment patch, which comprises:

a patch body having a contacting surface for placing on a skin surface of treating tissues of a user;

a dressing layer which is provided on the contacting surface containing positively charged metallic ions for depolarizing negative ions accumulated under the skin surface of the treating tissues; and a far infrared ray emitter disposed on the patch body for emitting far infrared rays penetrating into the treating tissues through the skin surface so as to provide an ion passway between the skin surface in contact with the dressing layer of the patch body and the treating tissues so as to enhance the depolarization of the positively charged ions of the dressing layer with the negative ions around the treating tissues of the user.

The present invention also provides a process of making the treatment patch, which comprises the steps of:

(a) grinding a metallic element into a fine powder form;

(b) grinding a far infrared ray emitting element 30 into a fine powder form;

(c) mixing the metallic element and the radiation element together to form a mixing powder, wherein the ratio of the metallic element and the radiation element is 50:50 by weight; and (d) coating the mixing powder on a contacting surface of a patch body to form a dressing layer thereon.

DETAILED DESCRIPTION OF THE PREFERRED EMBODIMENT

It is well known that the body energy flows through meridians. Muskuloskeletal pain may occur when there is imbalance or blockage in energy flow through the body. The fact that electrically charged particles are dissolved in the fluid bathing all living cells alleges that the body generates its own bioelectromagnetic field. The membrane surrounding each cell contains microscopic pores through which ions can flow into or out of each cell. Ions can be actively moved across the cell membrane through such pores so the ions become concentrated on one side or the other. It is therefore an electrogenic pump as it produces a net movement of positive charge out of the each cell across each cell membrane that varies from −9 mV to −100 mV in different tissues. In human nerve cells the membrane potential averages around −70 mV. It is known that the membrane potential is related to passing messages from one cell to another, passing information along nerve cells and muscle cell contraction, including the heart beat.

Therefore, the movement of electrically charged ions in and out of cells is the main source of the body electrical field. The generation and maintenance of these bioelectrical fields also consume 70% of energy by using metabolic processes occurring the body.

When the muscle or joint feels pain, the bioenergetic cell functions of its body tissues may be affected as follows:
  (i) electrical transmission through nerves is increased when pain is perceived;
  (ii) transport of ions across cell membranes is altered during inflammation;
  (iii) damaged cells may leak positive ions, producing a slow and steady electric current;
  (iv) changes in the composition of blood, body fluids and salt balance will alter the body's normal electrical field.

Figure 1:
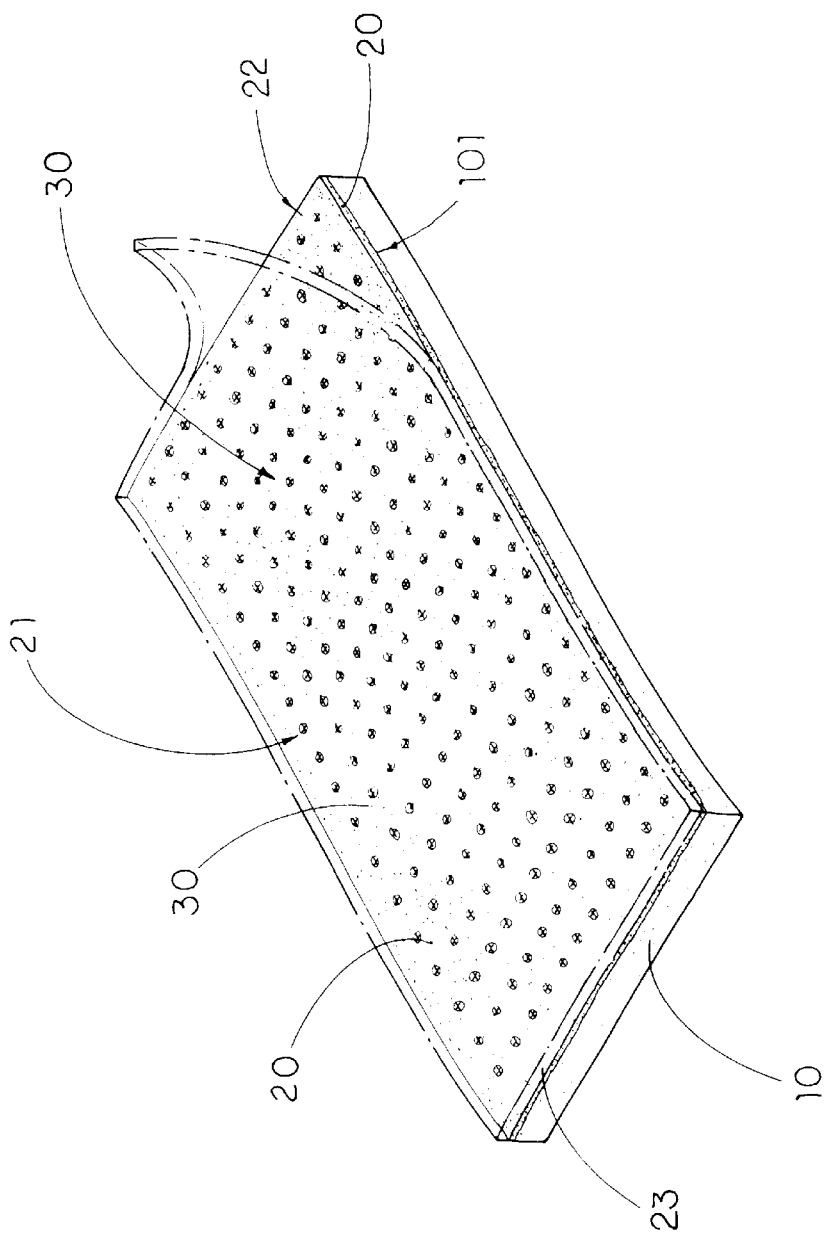
FIG. 1 is a perspective view of a treatment patch according to a preferred embodiment of the present invention.
Figure 2:
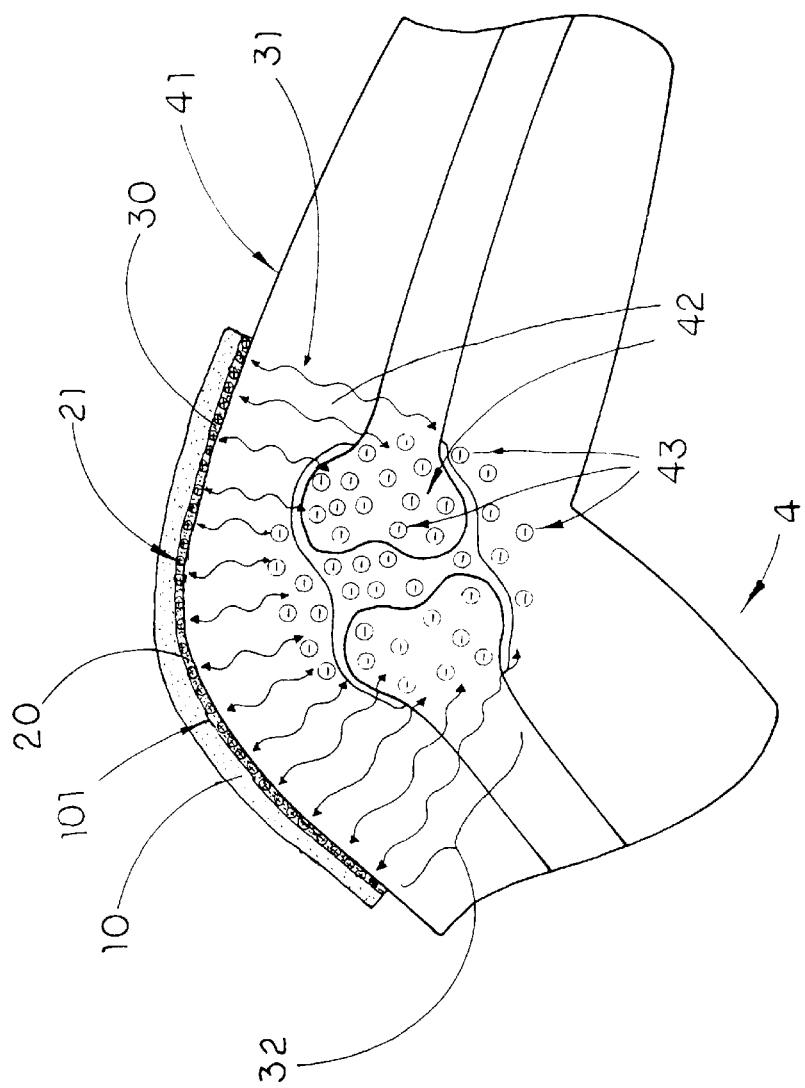
FIG. 2 is a sectional view of the treatment patch applied on a human body according to the above preferred embodiment of the present invention.
Figure 3:
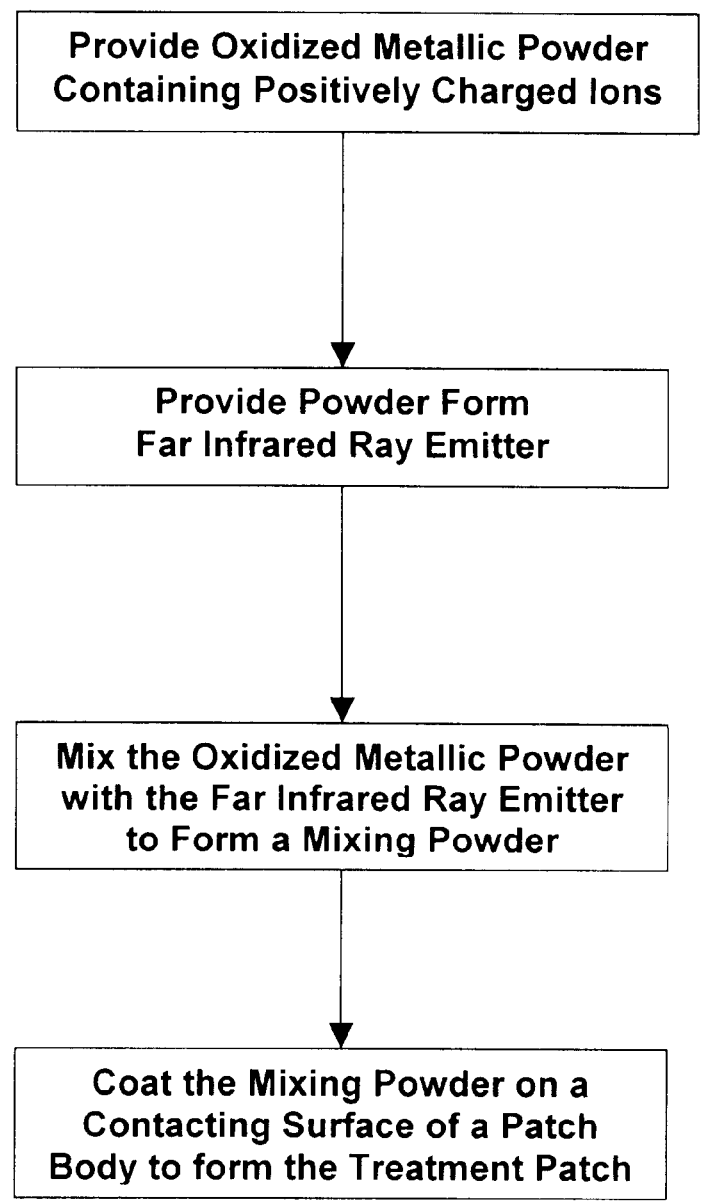
FIG. 3 is a flow chart illustrating the manufacturing process of the treatment patch according to the above preferred embodiment of the present invention.

Accordingly, negative ions are unusually found accumulating at the painful muskulo-skeletal tissues or tissues containing wound cells. Referring to FIGS. 1 to 3 of the drawings, according to a preferred embodiment of the present invention, a treatment patch loaded with a large quantity of positively charged ions is used for depolarizing the negative ions in a treating tissue of the muscle or joint to relieve muskulo-skeletal pain due to backache, toothache, osteoarthritis, tennis elbow, rheumatics, fibrositis, gout, sprained and torn muscles, and etc..

The treatment patch of the present invention comprises a sheet like patch body 10 which has a contacting surface 101 for placing on a skin surface 41 of a treating tissues 42 of a user 4.

A dressing layer 20 which is provided on the contacting surface 101 containing positively charged metallic ions 21 for depolarizing negative ions 43 accumulated under the skin surface 41 of the treating tissues 42. Moreover, a far infrared ray emitter 30 is disposed on the patch body 10 for emitting far infrared rays 31 penetrating into the treating tissues 42 through the skin surface 41 so as to provide an ion passway 32 between the skin surface 41 in contact with the dressing layer 20 of the patch body 10 and the treating tissues 42 so as to enhance the depolarization of the positively charged ions 21 of the dressing layer 20 with the negative ions 43 around the treating tissues 42 of the user 4.

The patch body 10 should be non-irritant and disinfectious since the patch body 10 may provide not only a soft surface in contact with human skin but also a disinfectious ability for preventing germs and skin disease from being infected. The patch body 10 can be made of fabric such as cotton.

The dressing layer 20 which is coated on the contacting surface 101 of the patch body 10 is a positive ion carrier. According to the preferred embodiment, the dressing layer 20 is made of powder form oxidized copper which is positively charged to form positive ions 21. It is worth to mention that other metallic elements such as zinc, gold or pure sliver can be used to substitute the copper to make the fine powder form positive ion carrier.

Billions of positively charged ions are loaded in the dressing layer 20, which is hundred and even thousand times more than the negative ions generally existed at the wound or painful tissues to be treated. However, the body skin and muscle between the treating tissues 42 and the treatment patch is an alterative obstacle of the depolarization of positive ions 21 and the negative ions 43.

Accordingly, an essential feature of the present invention is to include a kind of ion carrier, i.e. a far infrared ray emitter 30, on the patch body 10 to provide a passway between the skin surface 101 and the treating tissues 42 for the positive ions 21. The far infrared ray emitter 30 is made of a kind of ceramic material that emits the predetermined far infrared rays having a wavelength from 6 $\mu$m to 12 $\mu$m preferrably.

It is well known that the water wavelength is 6$\mu$m 14 $\mu$m and the bioelectromagnetic wavelength is about 6 $\mu$m. Therefore, the 6 $\mu$m–12 $\mu$m far infrared rays are capable of penetrating through the human skin and tissues and reaching the human tissues 3cm and more under the skin.

It is worth to mention that pain is transmitted along nerve cells as an electric signal. While quiescent, the nerve cell has a small charge of about −70 mV wherein a pain signal depolarizes the nerve cell. Besides, 80% of human body is composed of water which has a wavelength from 6 $\mu$m to 14 $\mu$m. Therefore, the far infrared ray 31 is capable of penetrating through the human skin and communicating with the nerve cell.

Moreover, scientists have proved that far infrared ray 31 is adapted for improving the human blood circulation and metabolism. Thus, when the far infrared rays 31 permeate into the human skin and tissues, the ion passway 32 is formed between the human skin and treating tissues to enhance the communication of the positive ions 21 and the negative ions 43 at the treating tissues 42.

In order to relief pain, the treatment patch is arranged to place on the human skin where the pain is located. Due to the present of the ion passway 32 created by the 6 $\mu$m–12 $\mu$m far infra-red rays 31, the depolarization rapidly proceeds via the ion passway 32 that the smaller amount of negatively charged ions 43 generated at the treating tissues 42 will be rapidly neutralized by the a lot more quantity of positive ions 21. When the negative ions 43 at the wound and inflamed treating tissues 42 is depolarized, tissue cells become normal and no electric pain signal is transmitted through nerves. Moreover, the far infrared rays 31 also enhance the human metabolism and blood circulation that provides substantially help to the muskulo-skeletal problems.

Referring to FIG. 3, the treatment patch of the present invention is produced by the following steps.
  (a) Provide the oxidized metallic powder containing positively charged ions 21 by grinding a predetermined amount of oxidized metallic element into a fine powder. It is preferred that the oxidized metallic powder is as fine as 1000 meshes.
  (b) Provide the far infrared ray emitter 30 by grinding a predetermined amount of far infrared ray emitting element into a fine powder.
  (c) Evenly mix the oxidized metallic powder with the far infrared ray emitter powder to form a mixing powder in a ratio of 50:50 by weight.
  (d) Coat the mixing powder on the contacting surface 101 of the patch body 10 by adhering to form the dressing layer 20.

In other words, according to the preferred embodiment as shown in FIGS. I to 3, the dressing layer 20 is made of the mixing powder of the positively charged ions 21 and the powder form far infrared ray emitter 30. The dressing layer 20 is coated on top of the contacting surface 101 of the patch body 10, wherein when the patch body 10 is made of cotton or other cloth material, the mixing powder is preferred to be immersed and stored in the fabric structure (as shown in FIG. 2). A thin adhesive layer 22 can be coated on top of the dressing layer 20 for adhering on the skin surface 41 of the user.

Alternatively, in step (c), the oxidized metallic powder and the far infrared ray emitter powder is preferred to also evenly mixed with a predetermined amount of adhesive to form the dressing layer 20, so that the dressing layer 20 can be simply adhered on the patch body 10 in such a manner that the mixing powder is evenly distributed on the patch body 10 while the patch body 10 is made of fabric such as cotton, paper or even plastic sheet with a predetermined thickness.

A detachable protective sheet 23 covers the dressing layer 20 when it is not used.

Figure 4:
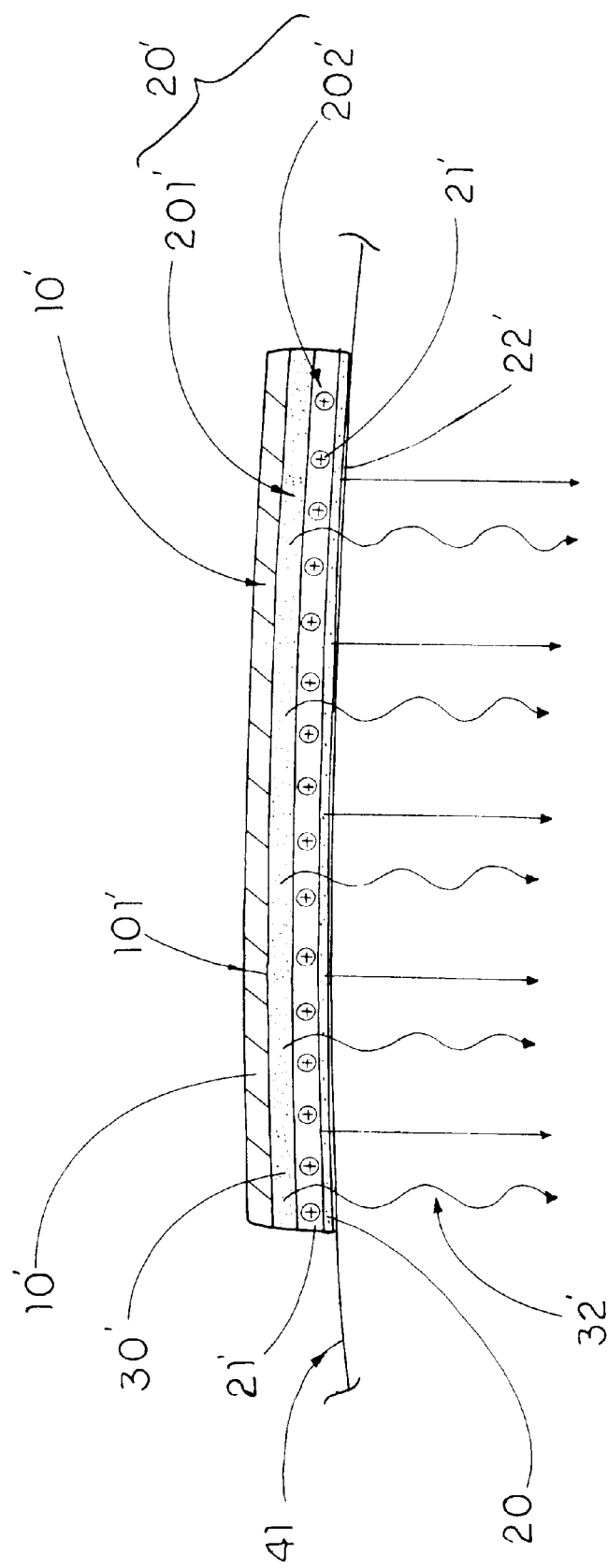
FIG. 4 illustrates an alternative mode of the treatment patch according to the above preferred embodiment of the present invention.

FIG. 4 illustrates an alternative mode of the treatment patch according to the above preferred embodiment, wherein the dressing layer 20' comprises a positive ion layer 201' and an ion carrier layer 202', wherein the positive ion layer 201' contains the oxidized metallic powder without the far infrared ray emitter powder 30 and the ion carrier layer 202', made of the far infrared ray emitter 30', is positioned between the positive ion layer 201 ' and the patch body 10'.

The treatment patch of this alternative mode is produced by the following steps.

(a) Provide the oxidized metallic powder containing positively charged ions 21' by grinding a predetermined amount of oxidized metallic element into a fine powder. It is preferred that the oxidized metallic powder is as fine as 1000 meshes.

(b) Provide the far infrared ray emitter 30' by grinding a predetermined amount of far infrared ray emitting element into a fine powder.

(c) Coat a predetermined thickness of the far infrared ray emitter 30' on the contacting surface 101' of the patch body 10' to form the ion carrier layer 202'.

(d) Coat a predetermined thickness of the oxidized metallic powder on the ion carrier layer 202' to form the positive ion layer 201', wherein the ion carrier layer 202' and the positive ion layer 201' integrally form the dressing layer 20'.

Similarly, a thin adhesive layer 22' can be coated on top of the positive ion layer 201' of the dressing layer 20'. for adhering on the skin surface 41 of the user. Alternatively, in step (d), the oxidized metallic powder can also be evenly mixed with a predetermined amount of adhesive to form the positive ion layer 201', so that the positive ion layer 201 ' can be simply adhered on the skin surface 41 of the user.

Moreover, according to the above preferred embodiment as shown in FIGS. 1 to 3 as well as the alternative mode thereof as shown in FIG. 4, the treatment patch may further comprise a medical layer 50 coated on top of the dressing layer 20, 20', which can contain other medicine such painkiller or Chinese medical herb in powder form adapted for permeating under the human skin to enhance the treatment effect.

It is worth to mention the positions of the positive ion layer 201' and the ion carrier layer 202', as well as the medical layer 50 can be inter-changed for relatively close fitting to the human skin.

What is claimed is:

1. A treatment patch, comprising:
a patch body which has a contacting surface for placing on a skin surface of treating tissues; and
a dressing layer which is provided on said contacting surface containing positively charged ions for depolarizing negative ions accumulated under said skin surface of said treating tissues, wherein a far infrared ray emitter is disposed on said patch body to emit far infrared rays penetrating into said treating tissues through said skin surface so as to provide an ion passway between said skin surface in contact with said dressing layer and said treating tissues so as to enhance said depolarization of said positively charged ions of said dressing layer with said negative ions at said treating tissues.

2. The treatment patch, as recited in claim 1, wherein said dressing layer made of a powder form oxidized metallic element which is positively charged to load with said positively charged ions.

3. The treatment patch, as recited in claim 2, wherein said far infrared ray emitted from said dressing layer has a wavelength of 6 $\mu$m to 12 $\mu$m.

4. The treatment patch, as recited in claim 3, wherein said far infrared emitter is made of a powder form ceramic material emitting said predetermined far infrared rays.

5. The treatment patch, as recited in claim 2, wherein said powder form oxidized metallic element which contains said positively charged ions is evenly mixed with said far infrared emitter and coated on said contacting surface of said patch body to form said dressing layer.

6. The treatment patch, as recited in claim 3, wherein said powder form oxidized metallic element which contains said positively charged ions is evenly mixed with said far infrared emitter and coated on said contacting surface of said patch body to form said dressing layer.

7. The treatment patch, as recited in claim 4, wherein said powder form oxidized metallic element which contains said positively charged ions is evenly mixed with said powder form ceramic material to form a mixing powder which is coated on said contacting surface of said patch body to form said dressing layer.

8. The treatment patch, as recited in claim 5, wherein 50% by weight of said oxidized metallic element is mixed with 50% by weight of said far infrared emitter.

9. The treatment patch, as recited in claim 6, wherein 50% by weight of said oxidized metallic element is mixed with 50% by weight of said far infrared emitter.

10. The treatment patch, as recited in claim 7, wherein 50% by weight of said oxidized metallic element is mixed with 50% by weight of said powder form ceramic material.

11. The treatment patch, as recited in claim 5, wherein said mixing powder is further mixed with a predetermined amount of adhesive to form said dressing layer.

12. The treatment patch, as recited in claim 6, wherein said mixing powder is further mixed with a predetermined amount of adhesive to form said dressing layer.

13. The treatment patch, as recited in claim 7, wherein said mixing powder is further mixed with a predetermined amount of adhesive to form said dressing layer.

14. The treatment patch, as recited in claim 10, wherein said mixing powder is further mixed with a predetermined amount of adhesive to form said dressing layer.

15. The treatment patch, as recited in claim 1, wherein said dressing layer comprises a positive ion layer and an ion carrier layer, wherein ion carrier layer is coated on said contacting surface of said patch body and said positive ion layer which is loaded with said positively charged ions is coated on said ion carrier layer.

16. The treatment patch, as recited in claim 2, wherein said dressing layer comprises a positive ion layer and an ion carrier layer, wherein ion carrier layer is coated on said contacting surface of said patch body and said positive ion layer which is loaded with said positively charged ions is coated on said ion carrier layer.

17. The treatment patch, as recited in claim 3, wherein said dressing layer comprises a positive ion layer and an ion carrier layer, wherein ion carrier layer is coated on said contacting surface of said patch body and said positive ion layer which is loaded with said positively charged ions is coated on said ion carrier layer.

18. The treatment patch, as recited in claim 4, wherein said dressing layer comprises a positive ion layer and an ion carrier layer, wherein ion carrier layer is coated on said contacting surface of said patch body and said positive ion layer which is loaded with said positively charged ions is coated on said ion carrier layer.

19. The treatment patch, as recited in claim 1, wherein said dressing layer comprises a positive ion layer and an ion carrier layer, wherein positive ion layer which is loaded with said positively charged ions is coated on said contacting surface of said patch body and said ion carrier layer is coated on said positive ion layer.

20. The treatment patch, as recited in claim 2, wherein said dressing layer comprises a positive ion layer and an ion carrier layer, wherein positive ion layer which is loaded with said positively charged ions is coated on said contacting surface of said patch body and said ion carrier layer is coated on said positive ion layer.

21. The treatment patch, as recited in claim 3, wherein said dressing layer comprises a positive ion layer and an ion carrier layer, wherein positive ion layer which is loaded with said positively charged ions is coated on said contacting surface of said patch body and said ion carrier layer is coated on said positive ion layer.

22. The treatment patch, as recited in claim 4, wherein said dressing layer comprises a positive ion layer and an. ion carrier layer, wherein positive ion layer which is loaded with said positively charged ions is coated on said contacting surface of said patch body and said ion carrier layer is coated on said positive ion layer.

23. The treatment patch, as recited in claim 5, further comprises an adhesive layer coated on top of said dressing layer.

24. The treatment patch, as recited in claim 6, further comprises an adhesive layer coated on top of said dressing layer.

25. The treatment patch, as recited in claim 7, further comprises an adhesive layer coated on top of said dressing layer.

26. The treatment patch, as recited in claim 18, further comprises an adhesive layer coated on top of said positive ion layer.

27. The treatment patch, as recited in claim 22, further comprises an adhesive layer coated on top of said ion carrier layer.

28. The treatment patch, as recited in claim 18, wherein said powder form oxidized metallic element is mixed with a predetermined amount of adhesive to form said positive ion layer.

29. The treatment patch, as recited in claim 22, wherein said powder form ceramic material is mixed with a predetermined amount of adhesive to form said ion carrier layer.

30. A process of making a treatment patch, comprising the steps of:
(a) providing an oxidized metallic powder containing positively charged ions;
(b) providing a powder form far infrared ray emitter that emits far infrared ray having a wavelength of 6 $\mu$m to 12 $\mu$m;
(c) mixing said oxidized metallic powder with said powder form far infrared ray emitter to form a mixing powder; and
(d) coating said mixing powder on a contacting surface of a sheet like patch body to form a dressing layer thereon.

31. The process as recited in claim 30 wherein, in the step (c), said oxidized metallic powder is mixed with said powder form far infrared ray emitter in a ratio of 50:50 by weight.

32. The process as recited in claim 30 wherein, in the step (c), said oxidized metallic powder and said far infrared ray emitter powder is mixed with a predetermined amount of adhesive to form said dressing layer.

33. The process as recited in claim 31 wherein, in the step (c), said oxidized metallic powder and said far infrared ray emitter powder is mixed with a predetermined amount of adhesive to form said dressing layer.

34. The process as recited in claim 31, after the step (d), further comprising a step of coating an adhesive layer on top of said dressing layer.

35. A process of making a treatment patch, comprising the steps of:
(a) providing an oxidized metallic powder containing positively charged ions;
(b) providing a powder form far infrared ray emitter that emits far infrared ray having a wavelength of 6 $\mu$m to 12 $\mu$m;
(c) coating a predetermined thickness of said far infrared ray emitter on a contacting surface of a patch body to form an ion carrier layer; and
(d) coating a predetermined thickness of said oxidized metallic powder on said ion carrier layer to form a positive ion layer, wherein said ion carrier layer and said positive ion layer integrally overlapped to form a dressing layer.

36. The process as recited in claim 35 wherein, in the step (d), said oxidized metallic powder is mixed with a predetermined amount of adhesive to form said positive ion layer.

37. The process as recited in claim 35, after the step (d), further comprising a step of coating an adhesive layer on top of said positive ion layer of said dressing layer.

38. A process of making a treatment patch, comprising the steps of:
(a) providing an oxidized metallic powder containing positively charged ions;
(b) providing a powder form far infrared ray emitter that emits far infrared ray having a wavelength of 6 $\mu$m to 12 $\mu$m;
(c) coating a predetermined thickness of said oxidized metallic powder on a contacting surface of a patch body to form a positive ion layer; and
(d) coating a predetermined thickness of said far infrared ray emitter on said positive ion layer to form an ion carrier layer, wherein said ion carrier layer and said positive ion layer integrally overlapped to form a dressing layer.

39. The process as recited in claim 38 wherein, in the step (d), said powder form far infrared ray emitter is mixed with a predetermined amount of adhesive to form said ion carrier layer.

40. The process as recited in claim 38, after the step (d), further comprising a step of coating an adhesive layer on top of said ion carrier layer of said dressing layer.

* * * * *